(12) United States Patent
Korte et al.

(10) Patent No.: US 8,563,748 B2
(45) Date of Patent: Oct. 22, 2013

(54) PROCESS FOR PREPARING SUBSTITUTED N-PHENYLHYDROXYLAMINES

(75) Inventors: Alexander Korte, Guaratingueta (BR); Michael Puhl, Hirschberg (DE); Marco Coppola, Goellheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/825,252

(22) PCT Filed: Sep. 20, 2011

(86) PCT No.: PCT/EP2011/066271
§ 371 (c)(1),
(2), (4) Date: Mar. 20, 2013

(87) PCT Pub. No.: WO2012/038392
PCT Pub. Date: Mar. 29, 2012

(65) Prior Publication Data
US 2013/0178634 A1    Jul. 11, 2013

Related U.S. Application Data

(60) Provisional application No. 61/384,748, filed on Sep. 21, 2010.

(30) Foreign Application Priority Data

Sep. 21, 2010  (EP) ................................. 10178045

(51) Int. Cl.
*C07D 231/22*  (2006.01)
(52) U.S. Cl.
USPC ......................................................... 548/371.1
(58) Field of Classification Search
None
See application file for complete search history.

(56) References Cited

U.S. PATENT DOCUMENTS 6,054,592 A *  4/2000  Muller et al. ............... 548/371.1

* cited by examiner

*Primary Examiner* — Kamal Saeed
(74) *Attorney, Agent, or Firm* — Brinks Hofer Gilson & Lione

(57) ABSTRACT

The present invention relates to a process for the preparation of a ring-substituted N-phenylhydroxylamine by reduction of the correspondingly substituted nitrobenzene compound, wherein the reduction is carried out by reacting the substituted nitrobenzene compound with hydrazine in the presence of a ruthenium catalyst.

15 Claims, No Drawings

PROCESS FOR PREPARING SUBSTITUTED N-PHENYLHYDROXYLAMINES

This application is a National Stage application of International Application No. PCT/EP2011/066271, filed Sep. 20, 2011, which claims the benefit of U.S. Provisional Application No. 61/384,748, filed Sep. 21, 2010, the entire contents of which are hereby incorporated herein by reference. This application also claims priority under 35 U.S.C. §119 to European Patent Application No. 10178045.0, filed Sep. 21, 2010, the entire contents of which is hereby incorporated herein by reference.

The present invention relates to a process for the preparation of substituted N-phenylhydroxylamines.

Substituted N-phenylhydroxylamines, in particular those carrying a substituent in the ortho position to the hydroxylamine group, are important precursors for the corresponding hydroxycarbamates and their O-substituted derivatives, which find use especially as fungicides. This class of fungicides, for which pyraclostrobine is a prominent representative, are disclosed, for example, in WO 93/15046 and WO 96/01256.

For the reduction of aromatic nitro compounds to N-phenylhydroxylamines several methods are available. Among those used on a technical scale reductions with metals, such as, for example zinc and amalgams have the drawback of having an adverse waste material balance, whereas, in comparison, heterogeneous hydrogenations using transition metals such as platinum or palladium as catalysts are considered favourable. In order to obtain reasonable selectivity for the N-phenylhydroxylamine these reactions have to be carried out in the presence of additives, such as sulfur compounds or organic bases, in particular amines, which partially poison or inactivate the catalyst (see for example EP 212375, WO 96/22967 and WO 99/12911). The use of these additives, however, may be accompanied by disadvantages, such as a diminished activity of the recycled catalyst after a few reaction cycles or difficulties with the removal of the additive during work-up, as removal of the additives by distillation is often not possible because of the thermal lability of the obtained N-phenylhydroxylamines. Moreover, the required transition metal catalysts are rather costly.

Alternatively the reduction can be accomplished by transfer hydrogenation using for example hydrazine or phosphinic acid as reducing agents in combination with one of the transition metals rhodium, iridium, nickel or palladium as catalyst (N. R. Ayyangar et al., Synthesis 1984, 938; I. D. Entwistle et al., Tetrahedron 1978, 34, 213 and P. W. Oxley et al., Organic Syntheses 1989, 67, 187). However, most publications dealing with the reduction of nitro benzene derivatives to the corresponding hydroxylamines by this approach describe only simple nitrobenzene derivatives as substrates. In addition, rhodium, which among the aforementioned transfer hydrogenation catalysts may result in the most selective conversions, is very expensive. So far, ruthenium has not yet been reported to show catalytic activity in transfer hydrogenations with hydrazine as reducing agent.

It is the object of the present invention to provide processes for preparing substituted N-phenylhydroxylamines that are easy to perform and are suitable for industrial scale production. These processes should additionally be inexpensive, in particular with regard to the catalyst, and be based on selective conversions.

The object is achieved by the processes described in detail below.

The present invention relates to a process for the preparation of a substituted N-phenylhydroxylamine which includes the reduction of the correspondingly substituted nitrobenzene compound. The reduction is carried out by reacting the substituted nitrobenzene compound with hydrazine in the presence of a ruthenium catalyst.

The process of the present invention is a kind of transfer hydrogenation, where the hydrazine compound acts as the reducing agent, the reaction being catalyzed by the ruthenium catalyst. In other words, the hydrogen atoms of the hydrazine compound are transferred to the nitro group of the substituted nitrobenzene compound, thereby reducing the nitro group ($NO_2$ group) of the substituted nitrobenzene compound to a hydroxylamine group (NHOH group).

The process according to the invention is associated with several advantages. For instance, the process of the invention allows the preparation of a wide array of differently substituted N-phenylhydroxylamines by a conversion that is high yielding and specific. The process is simple and inexpensive and can be handled efficiently also on the industrial scale. As a particular benefit the process of the invention provides effective means for preparing 2-pyrazoloxymethyl phenylhydroxylamine derivates that are important precursors for the corresponding fungicidally active carbamates. Moreover, the process according to the invention allows to obviate using difficult to remove additives.

With regard to substituted phenylhydroxylamine and substituted nitrobenzene, the term "substituted" is intended to mean that the phenyl rings of the substituted phenylhydroxylamine and substituted nitrobenzene carry one or more, e.g. 1, 2 or 3 substituents that is/are inert to the condition of the reductive conversion, in addition to the nitro group or the hydroxylamine group, respectively. Suitable substituents that is/are inert to the condition of the reductive conversion include, but are not limited to halogen, cyano, alkyl, haloalkyl, alkoxy, haloalkoxy, alkylcarbonyl, carboxyl, aminocarbonyl, alkylaminocarbonyl, dialkylaminocarbonyl, alkylcarbonylamino, alkoxycarbonyl, aryl, aryloxy, arylmethyl, aryloxymethyl, arylmethoxy, arylmethoxycarbonyl, arylvinyl, hetaryl, hetaryloxy, hetarylmethyl, hetaryloxymethyl, hetarylmethoxy, hetarylmethoxycarbonyl, hetarylvinyl, cycloalkyl, cycloalkoxy, cycloalkylmethyl, cycloalkoxymethyl, cycloalkylmethoxy, cycloalkylmethoxycarbonyl and cycloalkyl vinyl, wherein the aryl, hetaryl or cycloalkyl rings of the aforementioned substituents may themselves carry one or more substituents selected from cyano, halogen, alkyl, haloalkyl, alkoxy, haloalkoxy, alkylthio, alkylcarbonyl, alkoxycarbonyl, carboxyl, aminocarbonyl, alkylaminocarbonyl, dialkylaminocarbonyl, alkylcarbonylamino or phenyl which may be unsubstituted or substituted with one or more substituents selected from halogen, alkyl and haloalkyl.

The process of the invention is particularly well suited for preparing ring-substituted N-phenylhydroxylamines that carry at least one substituent in the ortho-position relative to the hydroxylamine group, and specifically for preparing ring-substituted N-phenylhydroxylamines of the general formula (I) from the corresponding nitrobenzene of the general formula (II),

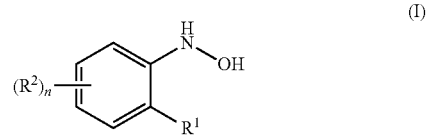

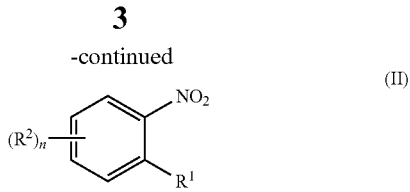

(II)

wherein
$R^1$ is selected from halogen, cyano, $C_1$-$C_4$-haloalkyl, $C_1$-$C_4$-alkoxy, $C_1$-$C_4$-haloalkoxy, $C_1$-$C_4$-alkylcarbonyl, $CO_2H$, $CONH_2$, $C_1$-$C_4$-alkylaminocarbonyl, di-($C_1$-$C_4$-alkyl)aminocarbonyl, $C_1$-$C_4$-alkylcarbonylamino, $C_1$-$C_4$-alkoxycarbonyl, and a group A-B, wherein
  A is —O—, —CH$_2$—, —O—CH$_2$—, —CH$_2$—O—, —CH$_2$—O—CO—, —CH=CH—, or a single bond, in particular A is —CH$_2$—O—, and
  B is phenyl, naphthyl, pyridinyl, pyrazinyl, pyrimidinyl, pyridazinyl, pyrazolyl, imidazolyl, oxazolyl, isoxazolyl, thiazolyl, isothiazolyl, 1,2,4-triazolyl, 1,2,3-triazolyl, furanyl, thienyl, pyrrolyl or $C_3$-$C_7$-cycloalkyl, wherein B may be unsubstituted or may carry 1 to 3 substituents $R^e$, in particular B is 3- or 4-pyrazolyl which carries an N-bond phenyl group which itself may be unsubstituted or substituted with 1, 2 or 3 substituents selected from halogen, $C_1$-$C_2$-alkyl and $C_1$-$C_2$-haloalkyl;
$R^e$ is cyano, halogen, $C_1$-$C_4$alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylcarbonyl, $C_1$-$C_4$-alkoxycarbonyl, $CO_2H$, $CONH_2$, $C_1$-$C_4$-alkylaminocarbonyl, di-($C_1$-$C_4$-alkyl)aminocarbonyl, $C_1$-$C_4$-alkylcarbonylamino, or phenyl which may be unsubstituted or substituted with 1, 2, 3 or 4 substituents selected from halogen, $C_1$-$C_4$-alkyl and $C_1$-$C_4$-haloalkyl;
$R^2$ is selected from halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-alkoxycarbonyl; and
n is 0, 1, 2 or 3, in particular 0.

In the context of the present invention, the terms used generically are defined as follows:

The term "ring substituted" characterizes a cyclic moiety, such as an aryl, hetaryl or cycloalkyl moiety, bearing one or more substituents, wherein the one or more substituents are attached to atoms within the carbocycle or the heterocycle and wherein the substituent is inert to the conditions of the reductive conversion according to the process of the invention.

The prefix $C_x$-$C_y$ denotes the number of possible carbon atoms in the particular case.

The term "halogen" denotes in each case fluorine, bromine, chlorine or iodine, especially chlorine or bromine.

The term "$C_1$-$C_4$-alkyl" denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "$C_3$-$C_7$-cycloalkyl" denotes monocyclic saturated hydrocarbon groups having 3 to 7 carbon ring members, such as cyclopropyl, cyclobutyl, cyclopentyl, cyclohexyl and cycloheptyl.

The term "$C_1$-$C_4$-haloalkyl", as used herein and in the haloalkyl units of $C_1$-$C_4$-halo-alkoxy, describes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroiso-propyl, 1-chlorobutyl, 2-chlorobutyl, 3-chlorobutyl, 4-chlorobutyl, 1-fluorobutyl, 2-fluoro-butyl, 3-fluorobutyl, 4-fluorobutyl and the like.

The term "$C_1$-$C_4$-alkoxy" denotes straight-chain or branched saturated alkyl groups comprising from 1 to 4 carbon atoms, which are bound via an oxygen atom to the remainder of the molecule. Examples of $C_1$-$C_4$-alkoxy are methoxy, ethoxy, n-propoxy, 1-methylethoxy (isopropoxy), n-butoxy, 1-methylpropoxy (sec-butoxy), 2-methylpropoxy (isobutoxy) and 1,1-dimethylethoxy (tert-butoxy).

The term "$C_1$-$C_4$-haloalkoxy" describes straight-chain or branched saturated haloalkyl groups comprising from 1 to 4 carbon atoms, which are bound via an oxygen atom to the remainder of the molecule. Examples thereof are chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, 1,1,2,2-tetrafluoroethoxy, 1-chloro-1,2,2-trifluoroethoxy, pentafluoroethoxy, 3,3,3-trifluoroprop-1-oxy, 1,1,1-trifluoroprop-2-oxy, 3,3,3-trichloroprop-1-oxy, 1-chlorobutoxy, 2-chlorobutoxy, 3-chlorobutoxy, 4-chlorobutoxy, 1-fluorobutoxy, 2-fluorobutoxy, 3-fluorobutoxy, 4-fluorobutoxy and the like.

The term "$C_1$-$C_4$-alkylcarbonyl" denotes alkyl radicals having from 1 to 4 carbon atoms which are bonded via a carbonyl group. Examples thereof are methylcarbonyl (acetyl), ethylcarbonyl, propylcarbonyl, isopropylcarbonyl, n-butylcarbonyl, sec-butylcarbonyl, isobutylcarbonyl and tert-butylcarbonyl.

The term "$C_1$-$C_4$-alkoxycarbonyl" denotes alkoxy radicals having from 1 to 4 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl.

The term "$C_1$-$C_4$-alkylaminocarbonyl" denotes a radical RHN—C(O)— in which R is $C_1$-$C_4$-alkyl, as defined above. Examples thereof are methylaminocarbonyl, ethylaminocarbonyl, propylaminocarbonyl, isopropylaminocarbonyl, n-butylaminocarbonyl, sec-butylaminocarbonyl, isobutylaminocarbonyl and tert-butylaminocarbonyl.

The term "di-($C_1$-$C_4$-alkyl)-aminocarbonyl denotes a radical RR'N—C(O)— in which R and R' independently of one another are $C_1$-$C_4$-alkyl, as defined above. Examples thereof are dimethylaminocarbonyl, diethylaminocarbonyl, methylethylaminocarbonyl, dipropylaminocarbonyl, ethylisopropylaminocarbonyl, methyl-n-butylaminocarbonyl, ethyl-sec-butylaminocarbonyl, n-butylisobutylaminocarbonyl and ethyl-tert-butylaminocarbonyl.

The term "$C_1$-$C_4$-alkylcarbonylamino" denotes a radical R—C(O)—NH— in which R is $C_1$-$C_4$-alkyl, as defined above. Examples thereof are formamido (formylamino), acetamido (acetylamino), propionamido and butyramido.

The term "$C_1$-$C_4$-alkylthio "($C_1$-$C_4$-alkylsulfanyl: $C_1$-$C_4$-alkyl-S—)" denotes straight-chain or branched saturated alkyl radicals having 1 to 4 carbon atoms which are bound via a sulfur atom to the remainder of the molecule. Examples for $C_1$-$C_4$-alkylthio include methylthio, ethylthio, propylthio, 1-methylethylthio, butylthio, 1-methylpropylthio, 2-methylpropylthio and 1,1-dimethylethylthio.

The remarks made below regarding preferred embodiments of the process according to the invention, especially regarding preferred meanings of the variables of the different reactants and products and of the reaction conditions of the process, apply either taken alone or, more particularly, in any conceivable combination with one another.

In the compounds of the formulae (I) and (II) the radical $R^1$ is preferably chlorine, bromine, $C_1$-$C_2$-alkyl, $C_1$-$C_2$-haloalkyl, $C_1$-$C_2$-alkoxycarbonyl or a group A-B, wherein A is —O—$CH_2$—, —$CH_2$—O— or a single bond, and B is pyrazolyl, imidazolyl, oxazolyl, isoxazolyl, thiazolyl, isothiazolyl, 1,2,4-triazolyl, 1,2,3-triazolyl or pyrrolyl, wherein B may be unsubstituted or may carry 1 or 2 substituents $R^e$. $R^1$ is more preferably chlorine, $C_1$-$C_2$-alkyl, $C_1$-$C_2$-haloalkyl or a group A-B, wherein A is —$CH_2$—O— and B is pyrazolyl, imidazolyl, 1,2,4-triazolyl, 1,2,3-triazolyl or pyrrolyl, wherein B may be unsubstituted or may carry 1 or 2 substituents $R^e$. Even more preferably $R^1$ is chlorine, methyl, chloromethyl, bromomethyl or pyrazolyloxymethyl, wherein the pyrazol ring may be unsubstituted or may carry 1 or 2 substituent $R^e$. Specifically, $R^1$ is methyl, chloromethyl, bromomethyl, pyrazol-3-yloxymethyl or pyrazol-4-yloxymethyl, where the pyrazole moiety in the last two substituents mentioned is unsubstituted or carries 1 or 2 substituents $R^e$.

In the definition of the radical B the substituent $R^e$ is preferably halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-alkoxycarbonyl or phenyl which may be unsubstituted or substituted with 1, 2 or 3 substituents selected from halogen, $C_1$-$C_2$-alkyl and $C_1$-$C_2$-haloalkyl. $R^e$ is more preferably chlorine, fluorine, $C_1$-$C_2$-alkyl, $C_1$-$C_2$-haloalkyl, $C_1$-$C_2$-alkoxycarbonyl or phenyl which may be unsubstituted or substituted with 1 or 2 substituents selected from chlorine, fluorine, methyl and halomethyl. Even more preferably $R^e$ is chlorine, fluorine, methyl and halomethyl, methoxycarbonyl or 4-chlorophenyl which may or may not carry one further substituent selected from chlorine, methyl and halomethyl.

In the compounds of the formulae (I) and (II) the variable n is preferably 0, 1 or 2 and especially preferably 0 or 1. When n is 1, $R^2$ is preferably in the para or meta position to the attachment point of the hydroxylamino group.

In the compounds of the formulae (I) and (II) the radicals $R^2$, if present, independently of one another are chlorine, bromine, $C_1$-$C_2$-alkyl, $C_1$-$C_2$-haloalkyl, $C_1$-$C_2$-alkoxy or $C_1$-$C_2$-haloalkoxy. $R^2$ are more preferably chlorine, $C_1$-$C_2$-alkyl or $C_1$-$C_2$-haloalkyl and even more preferably chlorine, methyl or halomethyl. Specifically, $R^2$ are 5-Cl, 4-Cl, 3-Cl, 5-methyl, 4-methyl, 3-methyl, 5-methoxy, 4-methoxy, 3-methoxy, 5-chloromethyl, 4-chloromethyl, 3-chloromethyl, 5-trifluoromethyl, 4-trifluoromethyl, 3-trifluoromethyl, 5-chloromethoxy, 4-chloromethoxy, 3-chloromethoxy, 5-trifluoromethoxy, 4-trifluoromethoxy, 3-trifluoromethoxy, 4,5-$Cl_2$, 3,4-$Cl_2$, 4,5-dimethyl, 3,4-dimethyl, 4,5-dimethoxy or 3,4-dimethoxy. The statements of position relate to the 1-position of the hydroxylamino group.

The process of the invention is particularly suitable for the preparation of substituted N-phenylhydroxylamines I that correspond to the following formula (I'),

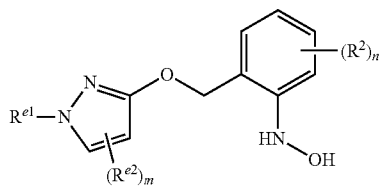

wherein
$R^{e1}$ is hydrogen or phenyl which may be unsubstituted or substituted with 1, 2, 3 or 4 substituents selected from halogen, $C_1$-$C_4$-alkyl and $C_1$-$C_4$-haloalkyl,
$R^{e2}$ is halogen $C_1$-$C_4$-alkyl or $C_1$-$C_4$-haloalkyl,
m is 0 or 1, and
$R^2$ and n are as defined herein before.

In the compounds of formula (I') preference is given to values for the variable n and to radicals $R^2$, if present, that have been mentioned as preferred herein before.

The radical $R^{e1}$ in the compounds of the formula (I') is preferably hydrogen or phenyl which may be unsubstituted or substituted with 1, 2 or 3 substituents selected from chlorine, fluorine, $C_1$-$C_2$-alkyl or $C_1$-$C_2$-haloalkyl. $R^{e1}$ is more preferably hydrogen or phenyl which may be unsubstituted or substituted with 1 or 2 substituents selected from chlorine, methyl or halomethyl. Specifically, $R^{e1}$ is hydrogen, 4-chlorophenyl, 3-chlorophenyl, 2-chlorophenyl, 4-methylphenyl, 3-methylphenyl, 2-methylphenyl, 4-methoxyphenyl, 3-methoxyphenyl, 4-chloromethylphenyl, 3-chloromethylphenyl, 4-trifluoromethylphenyl, 3-trifluoromethylphenyl, 3,4-dichlorophenyl, 2,4-dichlorophenyl, 3-methyl-4-chlorophenyl, 3-methoxy-4-chlorophenyl, 3-chloromethyl-4-chlorophenyl or 3-trifluoromethyl-4-chlorophenyl. The statements of position relate to the attachment point of the pyrazole ring in position 1 of the phenyl ring.

The variable m in the compounds of the formula (I') is preferably 0 or 1 and especially preferably 0. When m is 1, $R^{e2}$ is preferably attached to either the carbon atom in position 4 or in position 5 of the pyrazole ring.

The radical $R^{e2}$ in the compounds of the formula (I') is preferably, if present, halogen, $C_1$-$C_2$-alkyl, $C_1$-$C_2$-haloalkyl, $C_1$-$C_2$-alkoxy, $C_1$-$C_2$-haloalkoxy or $C_1$-$C_2$-alkoxycarbonyl. $R^{e2}$ is more preferably chlorine, fluorine, $C_1$-$C_2$-alkyl, $C_1$-$C_2$-haloalkyl or $C_1$-$C_2$-alkoxycarbonyl and even more preferably chlorine, fluorine, methyl, halomethyl or methoxycarbonyl.

The inventive transformations described hereinafter are performed in reaction vessels customary for such reactions, the reaction being configurable in a continuous, semicontinuous or batchwise manner. In general, the particular reactions will be performed under atmospheric pressure. The reactions may, however, also be performed under reduced or elevated pressure.

The process according to the invention for preparing substituted N-phenylhydroxyl-amines I comprises the conversion to a compound I via a catalytic transfer hydrogenation of the corresponding nitrobenzene compound of the formula (II),

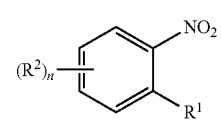

wherein the variables n, $R^1$ and $R^2$ have the meanings, including the preferred meanings, as defined herein before. The conversion is effected by reacting the nitrobenzene compound II with hydrazine as reducing agent in the presence of a ruthenium catalyst, preferably in a solvent, under suitable reaction conditions.

In the process according to the invention, hydrazine is understood to mean the hydrazine reactant, either as the anhydrous liquid, as hydrazine hydrate comprising about one molecule water per one molecule hydrazine ($N_2H_4 \cdot H_2O$) or as a solution, in particular an aqueous solution, preferably having a water content of 35 to 70% (w/w). Preference is given to using the hydrazine hydrate.

In the ruthenium catalyst which is used in the process of the present invention, ruthenium is the active metal or makes up at least 80% by weight, in particular at least 90% by weight of the total amount of active metal present in the catalyst. Active metal is the catalytically active metal, i.e. which is involved in the catalytic transfer hydrogenation mechanism.

Apart from ruthenium, the catalyst may contain one or more further active metals. These active metals may be present in amounts of up to 20% by weight based on the total amount of active metal, i.e. the total amount of ruthenium and further active metal. Further active metal include e.g. group VIIIb metals, group Ib metals and Group VIIb metals of the periodic table (CAS version), such as Pd, Pt, Rh, Fe, Co, Ni, Ir, Rh or Cu. Preferably ruthenium is the only active metal, i.e. ruthenium makes up at least 99% by weight of the active metal present in the catalyst.

The ruthenium catalyst used in the present invention may be a full catalyst or a supported catalyst. A full catalyst is a catalyst, where the active metal in its elementary or oxidic form makes up at least 50% by weight in particular at least 80% by weight of the catalyst in its active form. A supported catalyst is a catalyst where the active metal is supported on an inert support material. In a supported catalyst the amount of active metal is principally in the range from 0.05% by weight to 15% by weight, in particular from 0.1 to 10% by weight, based on the total amount of active metal and support material. Suitable support materials include active carbon, silicon carbide, silicon dioxide, titanium dioxide, zirconium dioxide, alumina, alumosilicates, such as zeolites. Preferably, the carrier material has a specific surface area, determined by $N_2$ adsorbtion according to DIN 66131, of at least 10 $m^2/g$, in particular from 20 to 1000 $m^2/g$. Preferably the carrier material is selected from the group consisting of silicon dioxide (silica), alumosilicates and alumina and mixtures thereof. In a particular preferred embodiment, the carrier material comprises at least 90% by weight, based on the weight of the carrier material, of alumina.

The catalyst, in particular the supported catalyst, may be in the form of large particles having a particle size of 1 to several millimeters, such as moulds, spheres or pellets, or in the form of finely divided particles having an average particle size of below 1000 μm, in particular below 800 μm such as a powder.

Preferably, the ruthenium catalyst is used in the form of finely divided particles. The choice of the average particle size of the catalyst depends, however, on several factors, such as the reactivity of the reactants used, whether neat ruthenium or supported ruthenium is used, and in case of supported ruthenium also on the ruthenium content of the catalyst as well as the carrier material used. In any event, the appropriate average particle size can be determined by the person skilled in the art in each individual case, for example by simple preliminary tests. The catalyst used in the process of the invention typically has a weight average particle size (weight average) in the range from 10 to 600 μm, preferably in the range from 20 to 200 μm.

It has been proven to be advantageous to activate the catalyst prior to its use in the process of the invention. Activation can be simply achieved by treating the catalyst with hydrogen. Generally, activation can be achieved at temperatures ranging from 0 to 500° C., in particular from 20 to 100° C., e.g. at ambient temperature (i.e. 20 to 30° C.). Activation can be achieved by treatment with pure hydrogen gas or by treatment with a mixture of hydrogen with one or more inert gases. Inert gases include e.g. nitrogen and noble gases such as argon or helium, and mixtures thereof. The partial hydrogen pressure in the gas used for activation will generally be in the range from 0.1 to 20 bar, in particular from 0.2 to 5 bar, e.g. at about 1 bar (0.9 to 1.1 bar). The time required for activation will generally depend from partial hydrogen pressure and activation temperature and will usually require from 10 min to 10 h, in particular from 0.5 to 5 h. Activation can be done immediately prior to the process of the invention. It is, however, also possible to activate the catalyst and to store the activated catalyst under inert atmosphere for a prolonged time period.

The reactants and the catalyst can in principle be contacted with one another in any desired sequence. For example, the nitrobenzene compound II, if appropriate in dissolved or dispersed form, can be initially charged and admixed with the hydrazine or, conversely, the hydrazine, possibly in dissolved or dispersed form, can be initially charged and admixed with the nitrobenzene compound II. Alternatively, the two reactants can also be added simultaneously to the reaction vessel. The ruthenium catalyst is added before or after the addition of one of the reactants or else together with one of the reactants, either in the form of a suspension or in bulk.

It has been found to be appropriate to initially charge the reaction vessel with the nitrobenzene compound II as such, in dispersed form or preferably in dissolved form, then add the ruthenium catalyst, as such or in suspended form, and subsequently the hydrazine. It is preferred to add the hydrazine gradually over a period of time in order to avoid its accumulation in the reaction mixture. The hydrazine is employed as such or in dissolved form.

Suitable solvents for dissolving or dispersing the reactants are preferably organic solvents that are inert toward the reactants. The choice of the solvent for the conversion in the process of the invention therefore depends on the particular reactants and reaction conditions selected in an individual case. It has generally been found to be advantageous to use an aprotic organic solvent for the conversion of the process of the invention. Useful aprotic organic solvents here include, for example, aliphatic $C_3$-$C_8$-ethers, such as diethyl ether, diisopropyl ether, dibutyl ether, isobutyl methyl ether, methyl tert-butyl ether (MTBE), ethyl tert-butyl ether (ETBE), 1,2-dimethoxyethane (DME) and diethylene glycol dimethyl ether (diglyme), halogenated aliphatic hydrocarbons such as methylene chloride, trichloromethane, dichloroethane and trichloroethane, aliphatic hydrocarbons, such as pentane, hexane, heptane, octane and also petroleum ether, cycloaliphatic hydrocarbons, such as cyclopentane and cyclohexane, alicyclic $C_3$-$C_6$-ethers, such as tetrahydrofuran (THF), tetrahydropyran, 2-methyltetrahydrofuran, 3-methyltetrahydrofuran and 1,4-dioxane, aromatic hydrocarbons, such as benzene, chlorobenzene, anisole, toluene, the xylenes and mesitylene, and mixtures of these solvents with one another.

Preferably the organic solvent for the conversion of the inventive process is selected from aliphatic $C_3$-$C_8$-ethers, such as diisopropyl ether, isobutyl methyl ether, ETBE and MTBE, halogenated aliphatic hydrocarbons, such as methylene chloride, alicyclic $C_3$-$C_6$-ethers, such as tetrahydrofurane (THF) and 1,4-dioxane, and aromatic hydrocarbons, such as chlorobenzene and toluene, and mixtures thereof. More preferably the organic solvent is selected from aliphatic $C_3$-$C_8$-ethers, such as diisopropyl ether, isobutyl methyl ether and MTBE, and alicyclic $C_3$-$C_6$-ethers, such as THF and 1,4-dioxane, and in particular from MTBE and THF. For instance, initially the nitrobenzene compound II may be charged to the reaction vessel solved in an aliphatic ether and after addition of the ruthenium catalyst as such or as suspended in an aliphatic ether the hydrazine is added as such or as a solution in an aliphatic or an alicyclic ether.

The total amount of the solvent used in the conversion of the process according to the invention is typically in the range from 200 to 4000 g/mol and preferably in the range from 300 to 3000 g/mol, based in each case on the nitrobenzene compound II.

Preferably the concentration of the nitrobenzene compound II in the total reaction mixture is in the range of 5.0 to 35.0% (w/w), more preferably in the range of 8.0 to 25.0% (w/w), in particular in the range of 10.0 to 20.0% (w/w) and specifically in the range of 12.0 to 16.5% (w/w).

In a preferred embodiment of the invention, the conversion to the N-phenylhydroxyl-amine I is carried out by employing the hydrogenation agent hydrazine in an amount of 1.0 to 7 mol hydrazine, preferably in an amount of 1.1 to 5.5 mol hydrazine, more preferably in an amount of 2.5 to 4.5 mol hydrazine, in particular in an amount of 3.0 to 4.0 mol hydrazine and specifically in an amount of 3.2 to 3.7 mol hydrazine, in each case relative to 1 mol of the nitrobenzene compound II to be hydrogenated.

In another preferred embodiment of the invention, the conversion to the N-phenyl-hydroxylamine I is carried out by employing the ruthenium catalyst in an amount of $10^{-5}$ to $10^{-2}$ mol ruthenium, preferably in an amount of $10^{-4}$ to $10^{-2}$ mol ruthenium, more preferably in an amount of $2\times10^{-4}$ to $2.5\times10^{-3}$ mol ruthenium, particularly in an amount of $4\times10^{-4}$ to $10^{-3}$ mol ruthenium and specifically in an amount of $7\times10^{-4}$ to $9\times10^{-4}$ mol ruthenium, in each case based on 1 mol of the substituted nitrobenzene compound.

In general, the conversion of the process according to the invention is performed under temperature control. The transfer hydrogenation reaction is typically effected in a closed or open reaction vessel with stirring apparatus. The reaction temperature of the conversion depends on several factors, such as the activity of the catalyst or the reactivity of the reactants, and can be determined by the person skilled in the art in the individual case, for example by simple preliminary tests. In general, the conversion is performed at a temperature in the range from −20 to 150° C., preferably in the range from −10 to 100° C., more preferably in the range from 0 to 50° C. and specifically in the range from 20 to 25° C. Depending on the solvent used, the reaction temperature and on whether the reaction vessel possesses a vent, a pressure of generally 1 to 5 bar and preferably of 1 to 3 bar is established during the reaction.

According to one embodiment of the invention the reaction mixture of the conversion according to the inventive process is adjusted to a temperature within the aforementioned range, particularly within the range mentioned as preferred, only after the addition of the hydrazine to the mixture containing the nitrobenzene compound II and the ruthenium catalyst has been completed, whereas during the addition of the hydrazine the temperature is kept in the range from −30 to 140° C., preferably in the range from −20 to 90° C., more preferably in the range from −10 to 40° C. and specifically in the range from 10 to 20° C.

The work-up of the reaction mixtures obtained in the hydrogenation reaction according to the invention and the isolation of the substituted N-phenylhydroxylamine I are effected in a customary manner, for example by a work-up routine which includes removal of the catalyst from the reaction mixture, e.g. by filtration. Further steps, which might be included in the work-up routine are removal of a possible aqueous layer, aqueous extractive work-up, removal of the solvent, for example under reduced pressure, or a combination of these measures. Generally, substituted N-phenylhydroxylamines I are obtainable in sufficient purity by applying such measures or a combination thereof. Thus, additional purification steps are usually not necessary and often should also be avoided as many hydroxylamines I are rather labile. If desired, however, further purification can be effected by methods commonly used in the art, such as chromatography.

Preferably, for work-up, the catalyst is removed from the reaction mixture, e.g. by filtration, an aqueous layer that possibly has been formed may or may not be removed and after drying and concentrating of the remaining mixture the crude substituted N-phenylhydroxylamine I is obtained. The product thus isolated can subsequently be retained for uses or sent directly to a use, for example use in a further reaction, or be purified further beforehand.

It is a particular benefit of the invention that the catalyst is not or not significantly poisoned during the transfer hydrogenation and hence, the catalyst can be used in one or more subsequent runs, if the reaction is performed batch-wise, i.e. the catalyst can be recycled. Moreover, this particular benefit allows to perform the reaction continuously, because no significant activity loss occurs during transfer hydrogenation.

In case the substituted N-phenylhydroxylamine I is intended to be subjected to a further reaction it is preferably employed as the crude product that is obtained directly after the aforementioned work-up procedure without additional purification. The crude product may contain as impurities unreacted nitrobenzene compound II. However, these impurities, if present, usually do not interfere with subsequent reactions and, in the event they are converted in such reactions at all, lead to reaction products that can be easily removed from the desired product. In the process of the present invention, over-reduction to the corresponding aniline does not noticeably occur and hence, the corresponding aniline compound will not be formed in noticeable amounts. Moreover, the process allows to perform the reaction in a manner that the formation of the aniline compound can be reduced to an extent which does not play any role in subsequent reactions.

The nitrobenzene compounds II used as starting compounds in the conversion of the process according to the invention are either known in the art or they can be prepared by analogy to standard methods of organic chemistry, or else can be prepared in analogy to the procedures described for example in WO 96/01256 and WO 93/15046.

According to a preferred aspect of the invention the process of the invention is used for preparing substituted N-phenylhydroxylamines I that are crucial intermediates for the synthesis of 2-(pyrazol-3'-yloxymethylene)-anilides, as described for example in WO 93/15046 and WO 96/01256. Such anilides are useful crop protection agents having fungicidal activity.

In another preferred aspect of the invention the N-phenylhydroxylamines I' are converted to fungicidal 2-(pyrazol-3'-yloxymethylene)-anilides via a 2-step process, including:

N-acylation using an alkyl haloformate, such as in particular methyl haloformate, to obtain a hydroxycarbamate compound of the formula (III'), wherein $R^3$ represents an alkyl group, preferably a methyl group, and the variables n, m, $R^2$, $R^{e1}$ and $R^{e2}$ are as defined herein before;

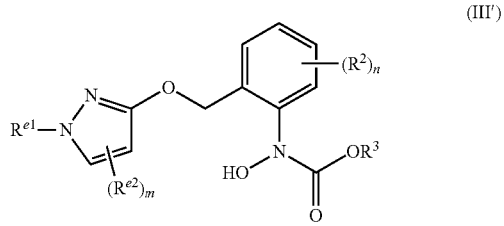

(III')

followed by an alkylation of the hydroxycarbamate compound III' to obtain the anilide compound IV',

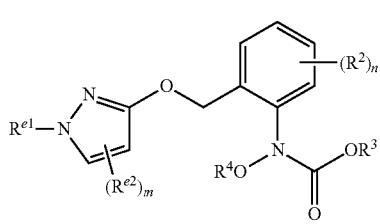

wherein $R^4$ represents an alkyl group, preferably a methyl group, and the variables n, m, $R^2$, $R^{e1}$, $R^{e2}$ and $R^3$ are as defined herein before;

In yet another preferred aspect of the invention the substituted N-phenylhydroxyl-amines I, wherein $R^1$ is a methyl group, are converted to crucial precursors IV''' en route to a more convergent synthesis of 2-(pyrazol-3'-yloxymethylene)-anilides in analogy to the synthesis described in WO 93/015046. Said conversion to the precursors IV''',

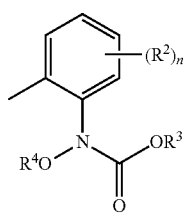

wherein the variables n, $R^2$, $R^3$ and $R^4$ are as defined herein before, can be accomplished in a 2-step process analogous to that of the aforementioned conversion of compounds I' to compounds IV'. In subsequent reaction steps compound IV''' is side-chain brominated and then coupled with a ring-substituted 3-hydroxypyrazole derivative to afford the desired 2-(pyrazol-3'-yloxymethylene)-anilides.

The above outlined conversions to compounds III', IV', III'' and IV''' can be carried out in analogy to the detailed procedures disclosed for example in WO 96/01256.

The process according to the invention allows the preparation, with a low level of complexity and in good yields and selectivities, of substituted N-phenylhydroxylamines I which are suitable starting compounds for preparing the 2-(pyrazol-3'-yloxymethylene)-anilides derived therefrom, such as those of the formula (IV').

EXAMPLES

Preparation of Ring-Substituted N-phenylhydroxylamines of the Formula (I)

General Method 12.5 mmol of a nitrobenzene compound II were suspended or dissolved in 22.3 ml of methyl tert-butyl ether (MTBE). To this suspension or solution were added 20 mg (0.08 mol %) of ruthenium on alumina (5% by weight) as a solid. After cooling the stirred mixture to 15° C. 2.2 g (44.0 mmol) hydrazine hydrate were added at that temperature over a period of 60 minutes. Afterwards stirring was continued for about 0.5 to 50 hours at a temperature of 25° C. until in process control by thin layer chromatography (dichloromethane) showed complete or nearly complete conversion of the nitrobenzene compound II. The reaction mixture was then filtered through a glass frit (class G4). The frit was then washed with 25 ml of MTBE. From the combined filtrates, a water layer, if present, was removed. The organic phase was dried over sodium sulphate and concentrated under reduced pressure. The crude product thus obtained was optionally purified by column chromatography.

Example 1

2-[1-(4-chloro-phenyl)-pyrazol-3'-oxymethyl]-N-hydroxy-aniline

The title compound was prepared by the general method using 2-[1-chloro-phenyl)-pyrazol-3'-oxymethyl]-1-nitrobenzene as starting material.

Reaction time at 25° C.: 7 hours

HPLC analysis indicated full conversion of the starting material and a purity of 98% of the obtained product without the necessity of further purification. The title compound was identified by $^1$H-NMR.

We claim:

1. A process for preparing a substituted N-phenylhydroxylamine by reduction of corresponding substituted nitrobenzene compound, wherein the reduction is carried out by reacting the substituted nitrobenzene compound with hydrazine in the presence of a ruthenium catalyst.

2. The process as claimed in claim 1, wherein the substituted N-phenylhydroxylamine carries at least one substituent in the ortho-position relative to the hydroxylamine group.

3. The process as claimed in claim 2, wherein the substituted N-phenylhydroxylamine is a compound of the formula (I),

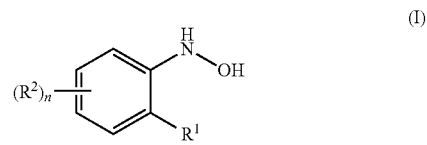

wherein $R^1$ is selected from the group consisting of halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylcarbonyl, $CO_2H$, $CONH_2$, $C_1$-$C_4$-alkylaminocarbonyl, di-($C_1$-$C_4$-alkyl)aminocarbonyl, $C_1$-$C_4$-alkylcarbonylamino, $C_1$-$C_4$-alkoxycarbonyl, and a group A-B, wherein A is —O—, —$CH_2$—, —O—$CH_2$—, —$CH_2$—O—, —$CH_2$—O—CO—, —CH=CH—, or a single bond, and B is phenyl, naphthyl, pyridinyl, pyrazinyl, pyrimidinyl, pyridazinyl, pyrazolyl, imidazolyl, oxazolyl, isoxazolyl, thiazolyl, isothiazolyl, 1,2,4-triazolyl, 1,2,3-triazolyl, furanyl, thienyl, pyrrolyl or $C_3$-$C_7$-cycloalkyl, wherein B may be unsubstituted or may carry 1 to 3 substituents $R^e$;

$R^e$ is cyano, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylcarbonyl, $C_1$-$C_4$-alkoxycarbonyl, $CO_2H$, $CONH_2$, $C_1$-$C_4$-alkylaminocarbonyl, di-($C_1$-$C_4$-alkyl)aminocarbonyl, $C_1$-$C_4$-alkylcarbonylamino, or phenyl which may be unsubstituted or substituted with 1, 2, 3 or 4 substituents selected from the group consisting of halogen, $C_1$-$C_4$-alkyl and $C_1$-$C_4$-haloalkyl;

$R^2$ is selected from the group consisting of halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-alkoxycarbonyl; and n is 0, 1, 2 or 3.

4. The process as claimed in claim 3, wherein $R^1$ is selected from the group consisting of halogen, $C_1$-$C_4$-alkyl, $C_1$-$C_4$-haloalkyl, and a group A-B.

5. The process as claimed in claim 3, wherein the substituted N-phenylhydroxylamine I is a compound of the formula (I'),

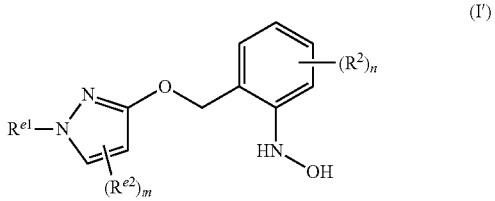

wherein $R^{e1}$ is hydrogen or phenyl which may be unsubstituted or substituted with 1, 2, 3 or 4 substituents selected from halogen and $C_1$-$C_4$-alkyl, $R^{e2}$ is halogen, $C_1$-$C_4$-alkyl and $C_1$-$C_4$-haloalkyl, m is 0 or 1.

6. The process as claimed in claim 1, wherein the catalyst is a supported catalyst comprising ruthenium which is supported on an inert support material.

7. The process as claimed in claim 6, wherein the support material is selected from the group consisting of carbon, alumina and silica.

8. The process as claimed in claim 6, wherein the catalyst has a ruthenium content of 0.1 to 10 percent by weight, based on the total weight of the catalyst.

9. The process as claimed in claim 8, wherein the catalyst has a ruthenium content of about 2 to 7 percent by weight, based on the total weight of the catalyst.

10. The process as claimed in claim 1, wherein the catalyst has a weight average particle size of 20 to 200 μm.

11. The process as claimed in claim 1, wherein the catalyst is employed in an amount of $10^{-4}$ to $10^{-2}$ mol ruthenium, based on 1 mol of the substituted nitrobenzene compound.

12. The process as claimed in claim 1, wherein a catalyst is employed which has been activated by treatment with hydrogen.

13. The process as claimed in claim 1, wherein the hydrazine is employed in an amount of 1.1 to 5.5 mol per 1 mol of the substituted nitrobenzene compound used.

14. The process as claimed in claim 1, wherein the concentration of the substituted nitrobenzene compound in the total reaction mixture is in the range of 8.0 to 25.0% (w/w).

15. The process as claimed in claim 1, wherein the reduction is carried out in an aprotic organic solvent.

* * * * *